United States Patent [19]
DeKosky et al.

[11] Patent Number: 5,773,220
[45] Date of Patent: Jun. 30, 1998

[54] DETERMINATION OF ALZHEIMER'S DISEASE RISK USING APOLIPOPROTEIN E AND α-1 ANTICHYMOTRYPSIN GENOTYPE ANALYSIS

[75] Inventors: Steven T. DeKosky; M. Ilyas Kamboh, both of Pittsburgh, Pa.

[73] Assignee: University of Pittsburgh, Pittsburgh, Pa.

[21] Appl. No.: 686,336

[22] Filed: Jul. 25, 1996

Related U.S. Application Data

[60] Provisional application No. 60/001,724 Jul. 28, 1995.

[51] Int. Cl.[6] .............................. C07H 21/04; C12Q 1/68; C12P 19/34; G01N 33/53
[52] U.S. Cl. .................................... 435/6; 435/7.1; 435/4; 435/91.2; 435/91.52; 536/23.5; 536/24.31; 536/24.33; 530/350; 935/9; 935/78
[58] Field of Search .......................... 435/6, 7.1, 4, 91.2, 435/91.52; 935/9, 78; 536/23.5, 24.32, 24.33; 530/350

[56] References Cited

U.S. PATENT DOCUMENTS 5,508,167  4/1996  Roses et al. ................................. 435/6

OTHER PUBLICATIONS

Faber et al. Journal of Hepatology 1993. 18:313–321.
Kamboh, Hum. Biol. 67:195–215, 1995.
Abraham et al., Cell 52:487–501, 1988.
Picken et al., J. Neuropathol. Exp. Neurol. 49:41–48, 1990.
Rozemuller et al., Acta Neuropathol. 82:200–207, 1991.
Shoji et al., Am. J. Pathol. 138:247–257, 1991.
Fraser et al., J. Neurochem. 61:298–305, 1993.
Ishiguro et al Virchows Archi. B. Cell Pathol. 64:221–227, 1993.
Wisniewski et al., Exp. Neurol. 110:121–126, 1990.
Matsubara et al., Ann. Neurol. 28:561–570, 1990.
DeKosky et al., Neurology 44:A354–355, 1994.
McKhann et al., Neurology 34:939–944, 1984.
Khachaturian, Arch. Neurol. 42:1097–1105, 1985.
Mirra et al., Neurology 41:479–486, 1991.
Eichner et al., Arteriosclerosis 10:379–385, 1990.
Randall et al., Science 243:1156–1159, 1989.
Matsubara et al., Ann. Neurol. 28:561–567, 1990.
Rayford et al., J. Neurochem. 58:88–94, 1992.
Wisniewski et al., Am. J. Pathol. 145:1030–1035, 1994.
Sanan et al., J. Clin Invest. 94:880–889, 1994.
Strittmatter et al., Exp. Neurol. 125:163–171, 1994.
Sanan et al., J. Clin. Invest. 94:860–869, 1994.
Nicoll et al., Nature Med. 1:135–137, 1995.
Abraham et al., Neurobiol. Aging 11:123–129, 1990.
Strittmatter et al., Proc. Natl. Acad. Sci. 90:1977–1981, 1993.
Kamboh et al., Atherosclerosis 112:145:149, 1995.
Ma et al., Nature 372:92–94, 1994.
Roses, Annals. Neurol. 38:6–14, 1995.
Saunders et al., Neurology 43:1467–1472, 1993.
Kamboh et al., Nature Genetics 10:486–488, 1995.
Kamboh et al., Ann. Neurol. 38:967–969, 1995.

*Primary Examiner*—Carla J. Myers
*Attorney, Agent, or Firm*—Baker & Botts, LLP

[57] ABSTRACT

The invention is directed to a method for screening for the risk of developing Alzheimer's disease (AD) in a subject by detecting the presence or absence of the APOE4 allele and the presence or absence of the ACT alleles which modify the risk of AD associated with the APOE4 allele. The invention offers a non-invasive method to identify individuals at high risk for the development of AD.

18 Claims, No Drawings

DETERMINATION OF ALZHEIMER'S DISEASE RISK USING APOLIPOPROTEIN E AND α-1 ANTICHYMOTRYPSIN GENOTYPE ANALYSIS

This invention was made with funding from the U.S. government, which has certain rights therein.

This application claims the benefit of U.S. Provisional Application No. 60/001,724, filed Jul. 28, 1995.

INTRODUCTION

The invention is directed to a method for screening for the risk of developing Alzheimer's disease (AD) in a subject by detecting the presence or absence of the APOE4 allele and the presence or absence of the ACT alleles which modify the risk of AD associated with the APOE4 allele. The invention offers a non-invasive method to identify individuals at high risk for the development of AD.

BACKGROUND OF THE INVENTION

Alzheimer's disease (AD) is a devastating neurodegenerative disorder. Genetic studies have identified the apolipoprotein E (apoE, protein; APOE, gene) gene as a strong susceptibility marker for AD (Strittmatter et al., Proc. Natl. Acad. Sci. USA 90:1977–1981, 1993; (Saunders et al., Neurology 43:1467–1472, 1993) and have demonstrated that the E4 allele of APOE is a major risk factor for AD regardless of age at onset or family history (for review see Kamboh, Hum. Biol. 67:195–215, 1995). However, the observation that the APOE4 allele, per se, is neither necessary nor sufficient for the expression of AD emphasizes the involvement of other environmental or genetic elements which, either in conjunction with APOE4 or alone, increase an individual's risk of developing AD.

Among other candidate genes which can affect the risk of this multifactorial disease is the gene coding for αl-antichymotrypsin (ACT). Like apoE, the ACT protein binds to β-amyloid peptide (ASP) (a 39–43 amino acid peptide present in amyloid deposits in the brains of AD patients) with high affinity in the filamentous deposits of AD plaques (Abraham et al., Cell 52:487–501, 1988; Abraham et al., Neurobiol. Aging 11:123–129, 1990; Picken et al., J. Neuropathol. Exp. Neurol. 49:41–48, 1990; Rozemuller et al., Acta Neuropathol. 82:200–207, 1991; Shoji et al., Am. J. Pathol. 138:247–257, 1991; Fraser et al., J. Neurochem. 61:298–305, 1993; Ma et al., Nature 372:92–94, 1994) and serves as a strong stimulatory factor in the polymerization of ASP into amyloid filaments (Ma et al., Nature 372:92–94, 1994).

In tissue samples from the brains of AD patients, the expression of ACT is enhanced, particularly in areas that develop amyloid plaques (Abraham et al., Cell 52:487–501, 1988; Abraham et al., Neurobiol. Aging 11:123–129, 1990; Picken et al., J. Neuropathol. Exp. Neurol. 49:41–48, 1990; Rozemuller et al., Acta Neuropathol. 82:200–207, 1991; Shoji et al., Am. J. Pathol. 138:247–257, 1991; Ishiguro et al., Virchows Archi. B. Cell Pathol. 64:221–227, 1993; Wisniewski et al., Exp. Neurol. 110:121–126, 1990). AD patients have higher levels of ACT in cerebrospinal fluid and in plasma than controls (Matsubara et al., Ann. Neurol. 28:561–570, 1990) and elevated ACT levels were detected in nondemented first-degree relatives of AD patients (Altstiel et al., Dementia 6:17–20, 1995). These studies suggest that ACT may play a role in the pathogenesis of AD.

SUMMARY OF THE INVENTION

The invention is directed to a method for screening for the risk of developing Alzheimer's disease in a subject by detecting the presence or absence of the APOE4 allele in combination with the presence or absence of the ACT alleles which modify the elevated risk of AD associated with the presence of the APOE4 allele in individuals.

The methods of the invention include the detection of APOE and ACT alleles by either nucleic acid analysis or by protein detection using assays which specifically identify the genotype (of apoE4 and ACT isoforms) of a subject and allow for an estimate of risk of developing AD based on such information. The invention allows the identification of individuals at increased risk of developing AD.

DETAILED DESCRIPTION OF THE INVENTION

The invention is directed to a method for screening for the risk of developing Alzheimer's disease (AD) in a subject by detecting the presence or absence of the APOE4 allele and the presence or absence of the ACT alleles which modify the risk of AD associated with the APOE4 allele. The invention offers a non-invasive method to identify individuals at high risk for the development of AD.

Apolipoprotein E (apoE) is a protein component of plasma lipoproteins, which plays a role in cholesterol metabolism. There are three principal isoforms of apoE, known as apoE2, apoE3 and apoE4, which are encoded by three alleles (APOE2, APOE3 and APOE4) at a single gene locus. An individual may have one of six different phenotypes of apoE, arising from expression of any two of the three alleles in the individual: three homozygous genotypes (apoE2/2; apoE3/3 and apoE4/4) and three heterozygous genotypes (apoE2/3; apoE2/4 and apoE3/4).

Presence of a single APOE4 allele in a subject is associated with more than 50% of late-onset sporadic cases of AD, with the age of onset of these cases being predominantly between the ages of 60 and 80. The homozygous APOE4 genotype is associated with the highest probability of development of AD.

The presence of the APOE alleles can be detected in an individual in a number of ways (e.g. PCR, LCR, RIA, and ELISA techniques), such as those described in U.S. Pat. No. 5,508,167 of Roses et al. issued Apr. 16, 1996, which is incorporated herein by reference.

The ACT gene is a single gene locus, located on chromosome 14. An ACT polymorphism with relevance to the elevated risk of developing AD in individuals with one or more APOE4 alleles is a substitution of alanine for threonine at the −15 position in the signal peptide resulting in two common alleles, ACT/A and ACT/T.

Individuals for which the diagnostic methods of the present invention may have particular relevance include those with a family history of AD, individuals with cognitive decline, elderly individuals, and all others whose history or symptomology suggest an inquiry into a diagnosis of AD or assessment of risk.

Biological samples which can serve as a source for the analysis of nucleic acid or protein for detection of both ACT and APOE polymorphisms include blood, cerebrospinal fluid (CSF) and tissue culture samples.

One method for the identification of ACT alleles includes the analysis of the genomic DNA of an individual to identify the ACT alleles by nucleic acid sequence. In this embodiment of the invention, the DNA may be amplified by, for example, polymerase chain reaction (PCR) or ligase chain reaction (LCR) or other techniques know in the art using primers designed to bind the ACT gene, for example, so as to amplify this gene during cycles of denaturation and polymerization (Chandra et al., Biochemistry 22:5055–5010, 1983). Upon amplification of a desired fragment of the gene, the amplified product may be analyzed by electrophoresis to confirm that a fragment of expected size has been generated, and the allele at the ACT gene may be identified using a nucleic acid probe capable of specifically hybridizing to the reaction product, in, for example, a Southern blot. Alternatively, the amplified fragment may be subjected to restriction enzyme analysis and electrophoresis which allows for the discrimination of alleles based on restriction pattern.

The ACT alleles may also be detected by reference to polymorphic genetic markers that are closely linked to the ACT locus and are reliably indicative of allele status, including, but not limited to, VNTR polymorphisms.

The ACT isoforms of the protein which correlate to the ACT/A or ACT/T alleles may be detected using immunologic assays that employ allele-specific antibodies such as those obtained by monoclonal antibody technique. For example, monoclonal antibodies to the ACT alleles may be produced using hybridoma cell lines as disclosed by Kohler and Milstein, Nature 265:495–497, 1975.

Antibodies, whether monoclonal or polyclonal, can be generated using a purified ACT immunogen, in particular an ACT protein produced by recombinant DNA means. The protein as antibodies may be produced by any number of species, including, but not limited to, mice, rabbits or humans. Immunoglobulins may be selected from IgG, IgM, IgA, IgD and IgE classes, and may be whole antibodies, fragments or single-chain antibodies, and may also be chimeric antibodies.

Signal generating moieties which may be used to tag an allele-specific antibody or a secondary antibody which binds to an allele-specific antibody include, but are not limited to, those derived from fluorescent dyes, radioisotopes and enzymes.

Immunologic assays which may be used to identify the ACT alleles in a biological sample from an individual include, but are not limited to, those performed in an ELISA or RIA format, preferably in a high-throughout manner suitable for clinical diagnostic studies. Other assays which can be used include Western blotting and immunoprecipitation.

Isoelectric focusing can also be used to resolve the proteins from a biological sample into discrete species which can be identified based on characteristic migration patterns.

The genotype of an individual is determined from the identification of the alleles found at each ACT locus. The individual may be homozygous—(A/A or T/T)—or may be heterozygous—(A/T) at the ACT locus.

According to the invention, determination of an individual's risk for developing AD is performed by analyzing the genotype of the individual with respect to both the APOE and ACT loci. As set forth supra, the presence of one APOE4 allele is associated with an increased risk of developing AD, with the risk particularly higher for those who are homozygous for the APOE4 allele. Analysis of an individual's ACT genotype provides a further refinement of the potential risk of developing AD in APOE4 positive individuals.

When an individual is determined to carry one or two APOE4 alleles (i.e. heterozygote or homozygote), the further identification of the ACT genotype possessed by that individual can be used to identify the degree of risk posed by the APOE4 allele(s). Where an individual is homozygous for the ACT/T allele (T/T), the gene dosage effect of the APOE4 allele is reduced. Where an individual is homozygous for the ACT/A allele (A/A), the gene dosage effect of the APOE4 allele is increased substantially (see Table 4 or Table 7). The risk of an individual developing AD based on carrying an APOE4 allele does not appear to be altered in an individual heterozygous for ACT (A/T).

It is also within the scope of the invention to analyze the levels of ACT protein in an individual, and utilize this information in an assessment of the risk of developing AD or to monitor the efficacy of treatments designed to reduce the progression of the pathology of AD. Such levels may be determined by, for example, RIA or ELISA assays.

Diagnostic kits containing reagents for use in an assay to directly detect ACT alleles (i.e. the DNA sequences encoding ACT) are within the scope of the invention. Such kits may contain primers which hybridize to a nucleic acid sequence corresponding to all or part of the ACT gene and allow amplification of such a sequence using such techniques as PCR, LCR or others known to those skilled in the art. Allele-specific probes which can be hybridize to such an amplified fragment and allow identification of the ACT allele(s) can be included, along with instructions for the use of the kit.

Diagnostic kits containing reagents that can be used to detect ACT isoforms (i.e. the ACT protein) are also within the scope of the invention. Such kits may include a solid support capable of binding the protein of interest (ACT), preferably through the protein's sulfhydryl groups, and further include one or more antibodies which are allele-specific and whose binding to a specific allele can be detected by the generation of a signal or the detection of a label. Other versions of a diagnostic kit include a kit comprising an allele-specific antibody attached to a solid support, capable of binding an antigen which is an ACT allele, and a means for detection of the antibody-antigen complex. Instructions for the use of such kits can also be included.

The practice of the invention employs, unless otherwise indicated, conventional techniques of recombinant DNA technology, protein chemistry, microbiology and genetics which are within the skill of the art. Such techniques are explained fully in the literature. See, e.g., *Current Protocols in Molecular Biology*. Ausubel et al., eds., John Wiley & Sons, Inc., New York, 1995.

The invention is illustrated by reference to the following non-limiting examples.

EXAMPLE 1

Relative Risk Determination of AD Based on APOE and ACT Alleles—Study 1

METHODS

Patients. American Caucasian AD patients (n=225) with mean age 74.6±0.6 (age range 22–101) were recruited from the University of Pittsburgh Alzheimer's Disease Research Center (ADRC). These include 109 (52 men and 57 women with mean age 75.8±0.9) autopsy confirmed and 116 (28 men, 88 women with mean age 73.5±0.7) clinically assessed cases of AD. Clinical diagnoses of the AD patients were made following a standardized evaluation, similar to that used in previous studies (DeKosky et al., Neurology 44:A354–355, 1994) consisting of medical history, general medical and neurological examination, psychiatric interview, neuropsychological testing and blood studies to rule out treatable causes of dementia. All cases were examined with MRI scan to rule out structural abnormalities of the brain. At a Consensus Conference, the examining neurologist and psychiatrist had to agree that the diagnosis was AD, utilizing the NINCDS/ADRDA (McKhann et al., Neurology 34:939–944, 1984) and DSM-III-R criteria (Diagnostic and Statistical Manual of Mental Disorders: DSM-III-R, 3rd revised ed., Washington, D.C. American Psychiatric Association, 1987). Neuropathological confirmation of the diagnosis of definite AD was made according to established criteria (Khachaturian, Arch. Neurol. 42:1097–1105, 1985; Mirra et al., Neurology 41:479–486, 1991).

Controls. Three control groups of American Caucasians were chosen to determine the distribution of ACT polymorphism in the general population. Of these 58 subjects (27 men, 31 women) with mean of 68.6±1.3 (age range 42–92) were selected from the University of Pittsburgh ADRC who underwent a similar evaluation of clinical and neuropathological diagnoses as described above for AD patients. The second group comprised 152 (71 men, 81 women) random and healthy controls from Denver, Colo. with a wide age range of 24–73 (mean age 50.5±0.8) (Kamboh et al., Atherosclerosis 112:145–159, 1995). The third group consisted of a narrow age range of 46–53 (mean age 48.7±0.2) of 105 healthy women from Pittsburgh, Pa. (Eichner et al., Arteriosclerosis 10:379–385, 1990).

Genetic Screenings. The APOE three-allelic polymorphism was screened using a PCR-based assay (Kamboh et al., Atherosclerosis 112:145–159, 1995). The ACT bi-allelic polymorphism in the signal peptide (−15 Ala→Thr) was determined by amplification of a 124 bp fragment. Forward primer 5'-CAG AGT TGA GAA TGG AGA-3' (SEQ ID NO: 1) and reverse primer 5'-TTC TCC TGG GTC AGA TTC-3' (SEQ ID NO: 2) were used for amplification in a 50 µl reaction mixture consisting of 1 µg genomic DNA, 0.3 µM of each primer, 0.24 µM of each dNTP (Pharmacia), 5 µl of 10X buffer (100 mM Tris-HCl pH 9.0, 500 mM KCl, 1% Triton X-100) and 1.25 U of Taq polymerase. After the denaturing step for 8 min at 94° C. the reaction mixture was subjected to 30 cycles consisting of 1 min at 94° C., 1.75 min at 55° C. and 2 min at 72° C. followed by one cycle at 72° C. for 5 min. The 124 bp fragment was digested overnight with BstNI (Biolabs, New England) according to manufacturer's instructions. The restriction fragments were resolved on 2% Nusieve agarose gel. The ACT/A (alanine) allele was characterized by two distinctive fragments of 84 bp and 33 bp. A single distinctive band of 117 bp was observed to denote the ACT/T (threonine) allele.

RESULTS

The distribution of ACT genotypes in AD cases and controls were in Hardy-Weinberg equilibrium (Table 1). The ACT A/A genotype was over-represented in AD patients compared to controls (35.1% vs 27.0%; p<0.02). The odds ratio for developing AD with two copies of the ACT/A allele (A/A genotype) was 1.5 [95% confidence interval (CI) 1.1–2.1; p=0.04] compared to one or no copy of the ACT/A allele (A/T or T/T genotypes). There was no effect of age on the distribution of ACT genotypes in the AD sample.

TABLE 1

Comparison of ACT genotype and allele frequencies between the control and AD groups

|  | Control Group[a] (n = 315) | AD Group[b] (n = 225) |
|---|---|---|
| ACT Genotype | n (%) | n (%) |
| A/A | 85 (27.0) | 79 (35.1) |
| A/T | 150 (47.6) | 97 (43.1) |
| T/T | 80 (25.4) | 49 (21.8) |
| ACT Allele Frequencies |  |  |
| ACT/A[c] | 0.508 | 0.567 |
| ACT/T | 0.492 | 0.433 |

[a]The control sample consists of three groups comprising 58 (mean age 68.6 ± 1.3) autopsy and clinically verified individuals, 152 (mean age 50.5 ± 0.8) random healthy subjects, and 105 (mean age 48.7 ± 0.2) middle age healthy women. There was no statistically significant difference in the distribution of ACT genotype and allele frequencies between these three groups.
[b]The AD sample consists of 109 (mean age 75.8 ± 0.9) autopsy confirmed and 116 (mean age 73.5 ± 0.7) clinically assessed cases. There was no statistically significant difference in the distribution of ACT genotype and allele frequencies between the two AD samples.
[c]Statistically significant between the control and AD groups, p = 0.055.

Studies were undertaken to investigate whether the risk conferred by the ACT A/A genotype was independent of the APOE polymorphism or whether these two loci acted synergistically to determine an individual's risk of developing AD. In controls the ACT A/A genotype was associated with low frequency of the APOE/4 allele compared to the other two genotypes of ACT (0.106 vs 0.180; p=0.01) (Table 2). The low frequency of the APOE4 allele in the ACT A/A genotype was at the expense of the APOE3 allele; with no effect on the APOE2 allele frequency. Similarly, the proportion of APOE 4/4 homozygous individuals was lower in the ACT A/A genotype (1.2%) compared to the ACT A/T (2.0%) and ACT T/T (3.8%) genotypes. However, a reverse trend was seen in the patient sample where the frequency of the APOE4 allele increased gradually from 0.337 in the ACT T/T genotype, 0.374 in the ACT A/T genotype to 0.417 in the ACT A/A genotype. The frequency of the APOE 4/4 homozygosity in the AD sample was highest in the ACT A/A genotype (16.7%) followed by the ACT A/T (11.6%) and ACT T/T (10.2%) genotypes.

TABLE 2

Comparison of APOE allele frequencies among the three ACT genotypes (A/A, A/T and T/T) between the control and AD groups

| APOE Alleles | Control Group | | | | AD Group | | | |
|---|---|---|---|---|---|---|---|---|
| | A/A (n = 85) | A/T (n = 149) | T/T (n = 79) | Total (n = 313)[a] | A/A (n = 78) | A/T (n = 95) | T/T (n = 49) | Total (n = 222)[b] |
| APOE2 | 0.076 | 0.091 | 0.101 | 0.089 | 0.038 | 0.037 | 0.031 | 0.036 |
| APOE3[c] | 0.818 | 0.721 | 0.734 | 0.751 | 0.545 | 0.589 | 0.633 | 0.583 |
| APOE4[c] | 0.106 | 0.188 | 0.165 | 0.160 | 0.417 | 0.374 | 0.337 | 0.381 |

[a]APOE data is missing on two individuals, one each in the A/T and T/T genotype.
[b]APOE data is missing on 1 and 2 individuals, respectively, in the A/A and A/T genotypes.
statistically significant between the ACT A/A genotype and the pooled ACT A/T and T/T genotypes, p = 0.01.

The ACT data was stratified based upon the presence or absence of the APOE4 allele (Table 3). The distributions of ACT genotypes and alleles were essentially identical in AD cases and controls who did not carry any copy of the APOE4 allele, but were significantly different between patients and controls who were carriers of the APOE4 allele. In the APOE4 carriers group, AD patients had significantly higher frequencies of the ACT A/A genotype (37.1% vs 18.3%; p<0.0001) and the ACT/A allele (0.586 vs 0.468; p=0.01) than in controls. In this group the odds ratio for developing AD with the ACT A/A genotype was 2.6 (95% CI 1.4–4.9; p<0.003).

TABLE 3

Comparison of distribution of ACT genotypes among non-APOE4 carriers (genotypes 3-3, 2-3, and 2-2) and APOE4 carriers (genotypes 4-4, 3-4 and 2-4) in AD patients and controls

| | Non-APOE4 Carriers | | APOE4 Carriers | |
|---|---|---|---|---|
| | AD Cases (n = 82) | Controls (n = 220) | AD Cases (n = 140) | Controls (n = 93) |
| | n (%) | n (%) | n (%) | n (%) |
| ACT genotypes | | | | |
| A/A[a] | 26 (0.317) | 68 (0.309) | 52 (0.371) | 17 (0.183) |
| A/T | 35 (0.427) | 96 (0.436) | 60 (0.429) | 53 (0.570) |
| T/T | 21 (0.256) | 56 (0.255) | 28 (0.200) | 23 (0.247) |
| ACT alleles | | | | |
| ACT/A[a] | 0.530 | 0.527 | 0.586 | 0.468 |
| ACT/T[b] | 0.470 | 0.473 | 0.414 | 0.532 |

[a]significant difference between AD cases and controls among the APOE4 carriers, p < 0.0001.
[b]significant difference between AD cases and controls among the APOE4 carriers, p = 0.01.

Since the difference in ACT genotype distributions was most dramatic in individuals carrying the APOE4 allele, an estimation was made of the relative risk of developing AD among ACT genotypes based upon the presence of one or two copies of the APOE4 allele (Table 4). Using APOE data alone, the odds ratio for developing AD with one and two copies of the APOE4 allele compared to no copy of the APOE4 allele was 3.5 (95% CI 2.4–5.0; P<0.0001) and 11.1 (95% CI 4.7–26.4; P<0.0001), respectively. However, while the risk associated with the APOE4 gene dosage was not modified by the ACT A/T genotype, it was significantly influenced by the presence of two copies of the ACT/A or ACT/T alleles. The ACT T/T genotype carried the same elevated risk with either one or two copies of the APOE4 allele; thus this genotype could be construed as protective from the added gene dosage effect of APOE4. However, in the presence of ACT A/A genotype, an individual's risk increased to almost two fold with one copy of APOE4 (3.5 vs 6.4) and to three fold with two copies of APOE4 (11.1 vs 34.0) beyond that which is associated with the APOE4 allele alone. The odds ratio was calculated by using the standard 2×2 table, according to conventional statistical analyses.

TABLE 4

Odds ratios for developing AD among ACT genotypes based upon the presence of one copy (genotypes E3-4 or E2-4) and two copies (genotype E4-4) of the APOE4 allele

| ACT genotypes | One copy of the APOE4 allele | Two copies of the APOE4 allele |
|---|---|---|
| | 3.5 (2.4–5.0; p < 0.0001)[a] | 11.1 (4.7–26.4; p < 0.0001) |
| T/T | 3.1 (1.4–6.8; p = 0.005) | 4.4 (1.0–20.1; p = 0.05) |
| A/T | 2.7 (1.5–4.7; p < 0.001) | 10.1 (2.7–38.3; p < 0.001) |
| A/A | 6.4 (3.1–13.4; p < 0.0001) | 34.0 (4.3–272.5; p < 0.001) |

[a]95% confidence interval with p-values in square parentheses.

EXAMPLE 2

Relative Risk Determination of AD Based on APOE and ACT Alleles—Study 2

METHODS

A further study was conducted that expands on and confirmed the results set forth above in Example 1.

Subjects. Control samples were obtained from two sources:
(1) a cohort from the San Luis Valley, Colo. (n=510) with an age range of 24–75 years and a mean of 52.5 years;
(2) a normal control cohort (n=69) from the University of Pittsburgh Alzheimer's Disease Research Center (ADRC) with an age range of 42–89 with a mean age of 67.1 years. Therefore, the total control sample consisted of 579 individuals, with a mean age of 54.2 years and an age range of 24–89 years.

The samples from patients with late onset, sporadic AD (n=308; mean age 75.0 years) were from the University of Pittsburgh ADRC and included 109 autopsy-confirmed definite AD, 175 probable AD, and 24 possible AD. Probable AD cases were patients seen at the University of Pittsburgh ADRC who met NINCDS-ADRDA criteria, as well as DSM-IIIR criteria for probable AD. The patients diagnosed with possible AD met the NINCDS-ADRDA criteria alone.

DNA from living patients was obtained from buffy coats isolated from blood; in the autopsied definite cases of AD, DNA was obtained from brain tissue using the Q1Aamp blood kit (QIAGEN Inc., Chatsworth, Calif.). Genetic screenings of the APOE and ACT polymorphisms were performed using specific polymerase chain reaction protocols as described in Example 1 above.

RESULTS

Allele Frequencies in the Control Population

Table 5 illustrates the distributions of the APOE and ACT polymorphisms for the total control cohort, as well as those for controls 60 years of age and older (n=199) and those for controls younger than 60 years of age (n=380). This analysis was undertaken to observe any age effect on allele frequency such as has been reported previously in APOE. In this large population, no differences were seen between the younger and older age groups. There were no allele frequency differences between the Colorado cohort and the ADRC cohort of controls and they were therefore combined for comparison to the AD group. There were no significant differences in the allele frequencies as a function of age above or below 60.

TABLE 5

Allele frequencies for APOE and ACT in the Control subjects, divided by age and expressed for the total control population.

|  | >60 (n = 199) | <60 (n = 380) | Total (n = 579) |
|---|---|---|---|
| Mean Age (range) | 67.5 (60–89) | 47.3 (24–59) | 54.2 (24–89) |
| ACT |  |  |  |
| A | .470 | .474 | .472 |
| T | .530 | .526 | .528 |
| APOE |  |  |  |
| E2 | .098 | .080 | .086 |
| E3 | .741 | .767 | .758 |
| E4 | .161 | .153 | .156 |

Allele Frequencies in the AD Population

The distribution of allele frequencies in the various groups with Alzheimer's disease is given in Table 6. In this table, the frequencies of the ACT alleles and the APOE alleles in the three diagnostic categories from which samples had been obtained were examined: definite, probable, and possible AD. Autopsy confirmed a clinical diagnosis of probable AD in 93% of cases from the University of Pittsburgh ADRC. In autopsy confirmation of possible AD cases at the University of Pittsburgh ADRC over the past ten years, clinical diagnoses of possible AD have turned out to be definite AD in greater than 90% of cases. The allele frequencies were similar among the three AD groups and therefore the combined data (n=310) were used for the calculations of relative risk.

TABLE 6

Allele frequencies for APOE and ACT in the AD subjects, divided by diagnosis and also summed for all AD cases. Note significant elevation of APOE4 allele frequencies compared to that of the normal control population (see Table 5).

|  | Definite AD (n = 109) | Probable AD (n = 175) | Possible AD (n = 24) | Total (n = 308) |
|---|---|---|---|---|
| Mean Age (range): | 76.4 (59–101) | 73.8 (47–94) | 77.8 (67–90) | 75.0 (47–101) |
| ACT |  |  |  |  |
| A | .560 | .546 | .583 | .551 |
| T | .440 | .454 | .417 | .449 |
| APOE |  |  |  |  |
| E2 | .032 | .023 | .063 | .029 |
| E3 | .587 | .646 | .583 | .621 |
| E4 | .381 | .331 | .354 | .350 |

Relative Risks

The AD patients had significantly higher frequency of the ACT A/A genotype (32.6% vs 22.4%; p<0.0001), and significantly lower frequency of the ACT T/T genotype (21.9% vs 28%; p<0.05) than controls. The odds ratio (OR) for AD of ACT A/A vs ACT T/T was 1.86 (95% C.I. 1.26–2.73; p<0.002). Table 7 presents the OR between APOE4 carriers and non-APOE4 carriers alone, as well as among the three ACT genotypes (T/T, A/T, and A/A), stratified based upon the presence of one or two copies of the APOE4 allele. The odds ratio of developing AD with a single copy of the APOE4 allele was 3.1 and that risk more than doubled (OR 7.4) with two copies of the E4 allele.

The relative risk associated with the APOE4 gene dosage effect was, however, changed when it was analyzed as a function of the ACT genotype. The ACT A/T genotype showed no significant difference from the relative risks of the APOE4 alone (OR 3.1 and 8.2 for one and two copies of the APOE4 allele, respectively). However, in those cases with an ACT T/T genotype, the risk of AD with the APOE 4/4 genotype was the same (OR=3.1) as that of a single APOE4 allele, thus eliminating the gene dosage effect of APOE4. Compared to the effect of the ACT T/T, the effect of the ACT A/A genotype on APOE4-induced risk was opposite: there was a slight increase in OR among individuals carrying one copy of the APOE4 allele (OR 4.0 vs 3.1) and 4–5 times higher in individuals carrying two copies of the APOE4 allele (OR 34.8 vs 7.4; see Table 7).

TABLE 7

Odds ratio of developing sporadic AD, utilizing the cases from the University of Pittsburgh Alzheimer's Disease Research Center. AD Cases = 308; Controls = 579.

|  | one copy of E4 3.1 (2.3–4.2; p < 0.0001)* | two copies of E4 7.4 (3.9–14.3; p < 0.001) |
|---|---|---|
| T/T | 2.4 (1.3–4.5; p – 0.004) | 3.1 (1.0–9.1; p < 0.04) |
| A/T | 3.1 (2.0–4.7; p < 0.001) | 8.2 (2.8–24.1; p < 0.0001) |
| A/A | 4.0 (2.2–7.2; p < 0.001) | 34.8 (4.4–273.9; p < 0.0007) |

*95% confidence interval with p-values in parentheses.

DISCUSSION

The above data show that the risk of AD conferred by APOE4 is significantly modified by genetic variation in the ACT gene. In the general American Caucasian population, approximately 1/50 individuals are homozygous for the APOE4 allele and approximately 1/4 are homozygous for the ACT/A allele, giving an estimated expected frequency of 1/200 individuals who will be homozygous at both polymorphic sites. In the control sample the frequency of this double homozygote was 1/313 compared to 1/17 (13 of 222)

in the AD case samples providing strong evidence that the combination of ACT A/A and APOE 4/4 is an extremely powerful susceptibility genotype for developing AD. Accordingly, those APOE 4/4 individuals who do not develop AD, even at older ages, likely do not carry the ACT A/A genotype and may well be ACT T/T, which appears to be a protective genotype. A possible explanation for the strong association of APOE4 carriers with the ACT A/A genotype with AD comes from the observation from the control sample which shows an interaction between the two genes. The mechanism of an interaction between the two genes giving rise to selection against individuals with the APOE 4/4 allele and ACT A/A genotypes is speculative at this stage but it may operate through some competing risks (e.g. heart disease or death from other causes).

The apparent synergistic effect of APOE4 and the ACT signal peptide polymorphism on risk of developing AD may operate through several possible mechanisms. Amino acid changes in the signal peptide can affect its hydrophobicity and alter post-translational protein processing and export (Randall et al., Science 243:1156–1159, 1989). The presence of the hydrophobic alanine instead of the hydrophilic threonine in the signal peptide of ACT may affect the translocation of ACT into the endoplasmic reticulum and eventually affect its secretion rate. The presence of alanine (ACT/A allele) may be associated with enhanced secretion of ACT into plasma as compared to the presence of threonine (ACT/T allele). This hypothesis is consistent with the observation that AD patients have higher levels of ACT in cerebrospinal fluid and in plasma than in controls (Matsubara et al., Ann. Neurol. 28:561–567, 1990; Rayford et al., J. Neurochem. 58:88–94, 1992).

Like apoE, the ACT protein also binds to ABP present in senile plaques of AD (Abraham et al., Cell 52:487–501, 1988; Abraham et al., Neurobiol. Aging 11:123–129, 1990; Picken et al., J. Neuropathol. Exp. Neurol. 49:41–48, 1990; Rozemuller et al., Acta Neuropathol. 82:200–207, 1991; Shoji et al., Am. J. Pathol. 138:247–257, 1991; Fraser et al., J. Neurochem. 61:298–305, 1993; Ma et al., Nature 372:92–94, 1994), and accelerates the polymerization of ABP into amyloid filaments (Ma et al., Nature 372:92–94, 1994).

If the ACT/A allele is associated with elevated ACT concentrations this, in conjunction with the APOE4 which is a major amyloid-promoting factor (Ma et al., Nature 372:92–94, 1994; Wisniewski et al., Am. J. Pathol. 145:1030–1035, 1994; Sanan et al., J. Clin Invest. 94:880–889, 1994), may induce ABP to form amyloid filaments much more rapidly. Alternatively, the ACT/A allele in the signal peptide is in strong linkage disequilibrium with a functional mutation affecting an amino acid substitution in the mature ACT protein which enhances the binding of the ACT protein to ASP, or interacts with apoE to alter binding to microtubular elements (Strittmatter et al., Exp. Neurol. 125:163–171, 1994).

Another mechanism relates to the potential interaction between ACT and APOE in the conversion of soluble amyloid to insoluble amyloid fibrils, which are a major pathological change in AD. In vitro studies indicate that while all three forms of APOE were able to convert soluble to insoluble amyloid fibrils, the APOE4 isoform was several times more efficient at this conversion of soluble amyloid, suggesting that the APOE4 allele could predispose to amyloid formation and deposition (Sanan et al., J. Clin. Invest. 94:860–869, 1994; Wisniewski et al., Am. J. Pathol. 145:1030–1035, 1994). This observation is consistent with the finding of more amyloid deposition in AD patients with APOE4 than AD patients without APOE4. In this same manner ACT was also able to convert soluble amyloid to insoluble amyloid fibers in the in vitro study (Ma et al., Nature 372:92–94, 1994). Thus, increased inflammatory activity or traumatic brain injury (which elevates both ACT and amyloid precursor protein) might both predispose to AD. This may contribute to the finding that APOE4 genotype has been reported to elevate the risk of developing AD after head injury (Nicoll et al., Nature Med. 1:135–137, 1995).

ApoE and the ACT protein bind to adjacent sites on the β-amyloid fragment, ACT binding to positions 1–12, and apoE binding to positions 12–28. The possibility must also be considered that interactions between apoE and the ACT protein may take place in their binding to the β-amyloid fragment, and that such interactions may influence the subsequent formation of insoluble amyloid fibrils. Notably, however, the ACT polymorphism occurring in the signal peptide does not have direct impact on the binding of ACT with the β-amyloid fragment. The ACT polymorphism may be in linkage disequilibrium with a functional mutation in the coding region of the ACT gene which directly affects this putative binding.

Similar effects of ACT modifying AD risk in a large cohort of familial AD patients from Indiana, a population separate from that of the Pittsburgh AD cohort, have also been seen (DeKosky et al., Neurology 46:A418, 1996, which is incorporated herein by reference).

The data indicate that the ACT polymorphism can modify the well-described risk of the APOE gene and appears to establish that interaction of two (or more) genes can influence the expression or phenotype of AD. These or other genes affecting the risk of AD conferred by APOE genotype also complicate the use of APOE alone in determining statistical risks of development of AD in asymptomatic patients and the likelihood of correct diagnosis in patients with a typical dementing course. The concept of polygenic risk determinants would account for the variable onset and course of AD, and would make it analogous to cardiac disease in this regard.

Various publications are cited herein, the contents of which are incorporated by reference in their entirety.

We claim:

1. A method of detecting if a subject is at increased risk of developing Alzheimer's disease (AD), comprising:
   detecting the presence or absence of one or two APOE4 alleles in the subject; and
   detecting the presence or absence of one or two ACT/A alleles in the subject; and
   determining if the subject is at increased risk of developing Alzheimer's disease, wherein the presence of one or two APOE4 alleles and two ACT/A alleles in the subject indicates that the subject is at increased risk for developing AD.

2. The method of claim 1, wherein detecting the presence or absence of ACT/A alleles is performed by DNA amplification.

3. The method of claim 2, wherein detecting the presence or absence of ACT/A alleles is performed by PCR.

4. The method of claim 2, wherein detecting the presence or absence of ACT/A alleles is performed by LCR.

5. The method of claim 1, wherein detecting the presence or absence of ACT/A alleles is performed by detection of ACT/A isoforms.

6. The method of claim 5, wherein the detection of ACT/A isoforms is performed by ELISA.

7. The method of claim 5, wherein the detection of ACT/A isoforms is performed by RIA.

8. A method for determining the prognosis of Alzheimer's disease (AD) in a subject, comprising:
   detecting the presence or absence of one or two APOE4 alleles; and
   detecting the presence or absence of one or two ACT/A alleles; and
   determining if the subject has a more negative prognosis for AD, wherein the presence of one or two APOE4 alleles and two ACT/A alleles in the subject indicates a more negative prognosis for AD.

9. The method of claim 8, wherein detecting the presence or absence of ACT/A alleles is performed by DNA amplification.

10. The method of claim 9, wherein detecting the presence or absence of ACT/A alleles is performed by PCR.

11. The method of claim 9, wherein detecting the presence or absence of ACT/A alleles is performed by LCR.

12. The method of claim 8, wherein detecting the presence or absence of ACT/A alleles is performed by detection of ACT/A isoforms.

13. The method of claim 12, wherein the detection of ACT/A isoforms is performed by ELISA.

14. The method of claim 12, wherein the detection of ACT/A isoforms is performed by RIA.

15. A method of detecting if a subject is at decreased risk of developing Alzheimer's disease (AD), comprising:
   detecting the presence or absence of two APOE4 alleles in the subject; and
   detecting the presence or absence of two ACT/T alleles in the subject; and
   determining if the subject is at decreased risk of developing Alzheimer's disease, wherein the increased risk due to the presence of two APOE4 alleles is decreased by the presence of two ACT/A/T alleles in the subject.

16. The method of claim 15, wherein detecting the presence or absence of the ACT/A alleles is performed by detection of ACT/A isoforms.

17. The method of claim 15, wherein the detection of ACT/A isoforms is performed by ELISA.

18. The method of claim 15, wherein the detection of ACT/A isoforms is performed by RIA.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:1:

CAGAGTTGAG AATGGAGA                      18

(2) INFORMATION FOR SEQ ID NO:2:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

TTCTCCTGGG TCAGATTC                      18